US007323565B2

(12) United States Patent
Wang et al.

(10) Patent No.: US 7,323,565 B2
(45) Date of Patent: Jan. 29, 2008

(54) METHOD FOR THE CATALYTIC PRODUCTION OF HYDROCODONE AND HYDROMORPHONE

(75) Inventors: Peter Xianqi Wang, Chesterfield, MO (US); Carl Ray White, St. Louis, MO (US)

(73) Assignee: Mallinckrodt Inc., Hazelwood, MO (US)

( * ) Notice: Subject to any disclaimer, the term of this patent is extended or adjusted under 35 U.S.C. 154(b) by 362 days.

(21) Appl. No.: 10/495,503

(22) PCT Filed: Nov. 5, 2003

(86) PCT No.: PCT/US03/35462

§ 371 (c)(1),
(2), (4) Date: May 13, 2004

(87) PCT Pub. No.: WO2005/047291

PCT Pub. Date: May 26, 2005

(65) Prior Publication Data

US 2006/0074239 A1    Apr. 6, 2006

Related U.S. Application Data

(60) Provisional application No. 60/425,360, filed on Nov. 11, 2002.

(51) Int. Cl.
C07D 489/02 (2006.01)
C07D 489/00 (2006.01)
(52) U.S. Cl. .............................. 546/45; 546/44; 546/46
(58) Field of Classification Search .................. 546/45, 546/44, 46
See application file for complete search history.

(56) References Cited

U.S. PATENT DOCUMENTS

| 2,544,291 | A | | 3/1951 | Baizer et al. |
| 2,577,947 | A | | 12/1951 | Baizer et al. |
| 2,628,962 | A | | 2/1953 | Homeyer et al. |
| 2,649,454 | A | | 8/1953 | Rapoport |
| 2,654,756 | A | | 10/1953 | Homeyer et al. |
| 2,715,626 | A | | 8/1955 | Pfister, III et al. |
| 4,003,903 | A | | 1/1977 | Schwartz |
| 4,322,426 | A | | 3/1982 | Hermann et al. |
| 4,368,326 | A | | 1/1983 | Rice |
| 4,478,840 | A | | 10/1984 | Smith, Jr. |
| 4,535,157 | A | | 8/1985 | Meltzer et al. |
| 4,613,668 | A | | 9/1986 | Rice |
| 5,571,685 | A | | 11/1996 | Hailes et al. |
| 5,847,142 | A | * | 12/1998 | Mudryk et al. ............... 546/45 |
| 6,177,567 | B1 | | 1/2001 | Chiu et al. |
| 6,235,906 | B1 | | 5/2001 | Sebastian |
| 2001/0005754 | A1 | | 6/2001 | Chiu et al. |
| 2001/0018519 | A1 | | 8/2001 | Sebastian |

FOREIGN PATENT DOCUMENTS

| DE | 365683 | 12/1922 |
| DE | 415097 | 6/1925 |
| DE | 607931 | 1/1935 |
| DE | 617238 | 10/1935 |
| DE | 623821 | 1/1936 |
| GB | PCT/GB97/01977 | 2/1998 |
| WO | WO 01/34608 | 5/2001 |

OTHER PUBLICATIONS

William S. Knowles, K. Ryoji Noyori, and Barry Sharpless; Information for the Public, the 2001 Nobel Prize in Chemistry: Mirror Image Catalysis; *Kungl Vetenskapsakademien*, The Royal Swedish Academy of Sciences; Apr. 8, 2002.

Bernard Demerseman, Ronan Le Lagadec, Benedicte Guilbert, Corinne Renouard, Pascale Crochet, and Pierre H. Dixneuf; Chelating and Hemilabile Properties of β- and γ- Keto Phosphines: ($\eta^6$-Arene) ruthenium (II) Derivatives from γ- Keto Phosphines and synthesis and Reactivity of Bis ($\eta^2$-keto phosphine-$P,O$) ruthenium (II) Complexes; *Advance ACS Abstracts*, Organometallics Vo. 13, No. 6, May 1, 1994.

Manuel M. Baizer, Kurt S. Ellner, and Athanasios Loter; The Rearrangement of Codeine to Dihydrocodeinone; *Journal of the American Pharmaceutical Association*, vol. XL, p. 580-582; Nov. 1951.

Annika Rimland, Goran Bergson, Ulf Obenius, Stefan Sjoberg, and Bengt Langstrom; *Synthesis of N-[Methyl-$^{11}$C] Hydromorphone by Using Multivariate Strategies for Optimization of Radiochemical Yields*; Appl. Radiat. Isol., vol. 38, No. 8, p. 651-654; 1987.

Katada, Masa; Yakugaku Zasshi, Morphine bases. III. Conversion of Phenylpseudocodeine, *Journal of the Pharmaceutical Society of Japan*; vol. 62, p. 347-355; Nippon Yakugakkai, Japan, 1942. This Article is relevant since it discloses that codeine was arranged to dihydrocodeinone in 50-79% yields using 10% Palladium black as catalyst, 6% Hydrochloric acid as medium, a temperature of 50-80oC and a current of hydrogen. But the reference is not involved in our claims on isomerization of codeine and morphine by a transition metal complex of a tertiary phosphine halid, [M(PR3)nXm]p. (Abstract is provided in English).

Nippon Yakugakkai; Electrolytic Reduction of Morphine and Codine; *Journal of the Pharmaceutical Society of Japan*; vol. 56, p. 44-52; Nippon Yakugakkai, Japan, 1936.This Article is relevant since it discloses electronic reduction of codeine and morphine to dihydrocodeine and dihydromorphine, respectively. But the reference is not involved in our claims on isomerization of codeine and morphine by a transition metal complex of a tertiary phosphine halid, $[M(PR_3)_nX_m]_p$. (Abstract is provided in English).

(Continued)

*Primary Examiner*—Charanjit S. Aulakh
(74) *Attorney, Agent, or Firm*—Sarah Pfeifer Vaz; Blackwell Sanders LLP

(57) ABSTRACT

A method for the catalytic conversion of codeine, morphine or analogs thereof into hydrocodone, hydromorphone or analogs thereof utilizing a transition metal complex of a tertiary phosphine halide as catalyst.

18 Claims, No Drawings

OTHER PUBLICATIONS

C. Mannich and H. Lowenheim; Archiv der Pharmazie; *Arch. Pharm.*; vol. 258, p. 295-316; 1920. This Article is relevant since it discloses reduction of codeinnone to dihydrocodeinone in the presence of Pd and hydrogen. But the reference is not involved in our claims on isomerization of codeine and morphine by a transition metal complex of a tertiary phosphine halid, [M(PR3)nXm]p. (Abstract is provided in English).

PCT International Search Report dated Jul. 12, 2004; International Application No. PCT/US03/35462; Applicant: Mallinckrodt, Inc.; International Filing Date Nov. 5, 2003.

Ninan, Aleyamma and Sainsbury, Malcolm (School of Chemistry, University of Bath, Claverton Down, Bath BA2 7AY, UK); An Improved Synthesis of Noroxymorphone; *Tetrahedron*, vol. 48, No. 32, pp. 6709-7616 (1992) (printed in Great Britain).

Rapoport, Henry; Naumann, Robert; Bissell, Eugene; and Bonner, Robert. *The Preparation of some Dihydro Ketones in the Morphine Series by Oppenauer Oxidation*; Oppenauer Oxidation in Morphine Series, pp. 1103-1107, Chemical Laboratory of the University of California, May 12, 1950, (Printed in Berkeley, California U.S.A.).

S.G. Davies et al.; Synthesis of 10(s)-Methyl-codeine & 20(s)-methyl-morphine; J. Chimie, 1980, p. 369-375.

Nathan L. Smith, Synthesis of Phenothiazine Derivatives for Use As Antioxidants, J. Org. Chem., 1950, 15, p. 1130.

J. Am. Pharm. Assoc., 1950, 40, p. 480.

S.G. Davies et al.; Palladium Catalyzed elaboration of Codeine & Morphine; J. Chem. Soc., Perkin Trans., 2001, 1, (12), p. 1413-1420.

* cited by examiner

METHOD FOR THE CATALYTIC PRODUCTION OF HYDROCODONE AND HYDROMORPHONE

CROSS REFERENCE TO RELATED APPLICATIONS

This application is a continuation of provisional application 60/425,360 filed Nov. 11, 2002.

FIELD OF THE INVENTION

The present invention relates to a method for the catalytic production of hydrocodone, hydromorphone, and analogs thereof, and more particularly to a method for catalytically converting codeine and morphine into hydrocodone and hydromorphone, respectively.

BACKGROUND OF THE INVENTION

Hydrocodone and hydromorphone are opioid analgesics having similar qualities to codeine and morphine. Conventional methods for producing hydrocodone and hydromorphone typically involve a two step oxidation/reduction route from codeine and morphine. Unfortunately, these methods are expensive and inefficient. Attempts to improve efficiency have included the use of catalytic methods. Known methods include the use of metallics, typically Ru, Rh, Pd and Pt on activated carbon as well as metallic complexes. The preparation of these catalysts is difficult, yields are poor, and isolation of the product is often burdensome.

Other catalytic methods, including the use of finely-divided platinum or palladium in an acidic media, are environmentally undesirable. Enzymatic methods of conversion have also been attempted, but as with the methods of catalysis discussed above, these methods are costly and difficult to scale up.

There is therefor a need for an improved method of conversion that is easily scaled up and economical for manufacturing purposes.

SUMMARY OF THE INVENTION

An aspect of the present invention is to provide a method for the catalytic conversion of a compound of Formula I into a compound of Formula II utilizing at least one transition metal complex of a tertiary phosphine halide as catalyst,

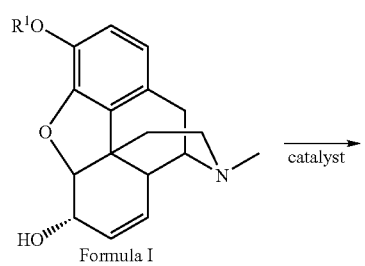

Formula I

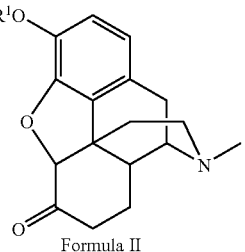

Formula II wherein $R^1$ is H, alkyl, aryl or acyl.

Another aspect of the present invention is to provide a one step method for the conversion of codeine or morphine into hydrocodone or hydromorphone, respectively.

These are merely illustrative aspects of the present invention and should not be deemed an all-inclusive listing of the innumerable aspects associated with the present invention. These and other aspects will become apparent to those skilled in the art in light of the following disclosure.

DETAILED DESCRIPTION

There is provided a method for the conversion of a compound according to Formula I to a compound according to Formula II,

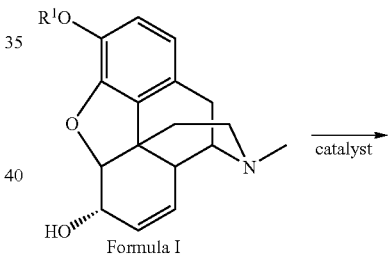

Formula I

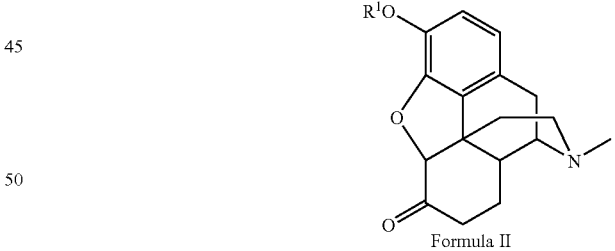

Formula II wherein $R^1$ is H, alkyl, aryl or acyl.

The method of the present invention is especially useful where $R^1$ is methyl or H, i.e., codeine or morphine, respectfully, leading to the formation of hydrocodone or hydromorphone, respectfully.

The transition metal catalysts of the present invention comprise a transition metal complex of a tertiary phosphine halide, $[M(PR^2{}_3)_n X_m]_p$, wherein M is preferably a Group VIII transition metal, $R^2$ is an alkyl or aryl, X is a halide or halide compound, n is 1, 2, 3 or 4, and m is 1 or 2. These complexes are capable of polymerizing, therefore p is at least 1. Preferred metals include Rh, Ru, Pd and Pt. The halide, X, is typically Cl or Br. Halide compounds include but are not limited to $BF_4$, $PF_6$, $ClO_4$, $CF_3SO_3$ and $OCOCF_3$. $R^2$ is an alkyl or aryl group, with phenyl being preferred. Many of these catalysts are commercially available, or are easily prepared as is known in the art.

In the above Formula I and Formula II alkyl groups useful therein include those having from about 1 to about 10 carbon atoms. Aryl groups in Formula I and Formula II include phenyl and substituted phenyl groups.

In one embodiment of the present invention the transition metal is Rh, and the metal complex is of the formula $[Rh(PR^2_3)_nX]_p$, wherein $R^2$ is an alkyl or aryl, X is a halide, n is 1, 2 or 3, and p is at least 1, or of the formula $[Rh(PR^2_3)_nY]_p$, wherein $R^2$ is an alkyl or aryl, n is 1, 2 or 3, p is at least 1 and Y is a halide compound, preferably including $BF_4$, $PF_6$, $ClO_4$ or $OCOCF_3$.

In another embodiment the transition metal is Ru and the metal complex is of the formula $[RuX_2(PR^2_3)_n]_p$ wherein $R^2$ is an alkyl or aryl, X is a halide, n is 1, 2, 3 or 4; and p is at least 1 or of the formula $[RuYX(PR_3^2)_n]_p$ wherein $R^2$ is an alkyl or aryl and wherein n=3, p is at least 1, Y=H and X=Cl; n=3, Y=H and X=H; n=4, X=H, Y=H; or n=2, 3 or 4, p is at least 1 and X=Y=$ClO_4$, $CF_3SO_3H$, $PF_6$ or $BF_4$.

A suitable method for producing a Ru complex of the present invention involves refluxing a Ru salt, for example $RuCl_3 \cdot xH_2O$ with an excess of triphenylphosphine in alcohol to form the complex $[Ru(P(C_6H_5)_3)_3Cl_2]_p$.

A Rh complex of the present invention is also commercially available, or can be prepared by refluxing rhodium trichloride with triphenylphosphine in alcohol, typically methanol or ethanol.

The catalytic conversion of the present invention has the further economic advantage of being able to convert a salt of codeine or morphine, for example codeine hydrochloride or morphine hydrochloride, to hydrocodone or hydromorphone, respectively.

The reaction of the present invention may be accomplished by any conventional process. A suitable process includes dissolving the reactant of Formula I in a suitable solvent in a reaction vessel. Suitable solvents include but are not limited to alcohols, preferably primary and secondary lower alkyl alcohols. The reaction vessel is then flushed with an inert atmosphere, typically nitrogen. The catalyst is added and the reaction mixture is refluxed under the inert atmosphere until the conversion is essentially complete, typically at least about an hour. The reaction mixture is cooled and crystals of the product are collected. The product may be purified by recrystallization in a suitable solvent as is well known in the art, or by any other suitable conventional method of purification.

In an alternative embodiment a tertiary amine, for example triethylamine, is added to the reaction mixture when the preferred Ru complex catalyst is used. The tertiary amine reduces the formation of side products, primarily the alkaloid neopine, a potential side product in reactions of the present invention utilizing the preferred Ru catalyst.

In another alternative embodiment the alkaloid compound is added to the reactants that form the catalyst and the catalyst formation reaction takes place in the presence of the alkaloid. The ability to form the catalyst and subsequently accomplish the catalytic conversion in the same reaction vessel further enhances the economy of the reaction.

EXAMPLES

Example 1

Codeine, 50.00 g, was dissolved in 200 ml methanol in a three-neck flask at room temperature. The flask was equipped with a condenser and nitrogen. The flask was flushed with nitrogen for five minutes with one neck opened. The catalyst, 0.50 g of $RhCl(P(C_6H_5)_3)_3$ was added to the solution. The flask was then flushed with nitrogen for another five minutes, and the open neck was closed. The reaction mixture was stirred under nitrogen and heated to reflux for four hours, then cooled to 0° C. for 30 minutes. The resulting crystals were removed by filtration. The collected crystals were washed four times with 10 ml cold methanol (5° C.), and dried in air for one hour yielding pale yellow crystals (41.50 g, yield 83%). The filtrate was pumped down to dryness to give 6.14 g yellow solid. The solid residue was dissolved in 40 ml refluxing methanol and cooled to 0° C. for 30 minutes and filtered. The collected crystals were washed four times with 3 ml portions of cold methanol (5° C.) and air dried for 2 hours yielding 3.41 g (6.8%) white crystals. HPLC analysis and NMR spectra confirm that the product is pure hydrocodone.

Example 2

Morphine, 50.00 g, was suspended in 500 ml methanol in a three neck flask equipped with condenser and nitrogen input and outlet. After refluxing under nitrogen for five minutes, one neck of the flask was opened. A catalyst, 0.50 g $RhCl(P(C_6H_5)_3)_3$ was added to the container. The opened neck was closed with a stopper. The reaction mixture was stirred under nitrogen and heated to reflux for 6 hours, cooled down to 0° C. for 30 minutes, and filtered. The collected solid was washed four times with cold methanol (5° C.) and dried in air for 20 minutes. The solid was kept under vacuum (15 mm Hg) at room temperature for 1 hour, yielding a white powder (38.83 g, yield 77.7%). The filtrate was distilled under nitrogen until only 200 ml of solution remained. It was cooled down to 0° C. for 30 minutes and filtered, yielding a white powder. The product was washed twice with 20 ml each and then once with 10 ml of cold methanol (5° C.) dried in air for 40 minutes to yield 3.48 g of a white powder product. HPLC analysis and NMR spectra confirm product is pure hydromorphone.

Example 3

Ruthenium dimer was prepared by refluxing 1 g $RuCl_3 \cdot xH_2O$ with 3 equivalents $P(C_6H_5)_3$ in EtOH (100 ml) overnight. The resulting catalyst, $[Ru(P(C_6H_5)_3)_2Cl_2]_2$ was obtained as a black precipitate after filtration, 63% yield.

Example 4

The catalyst of Example 3 was reacted with codeine in MeOH in the presence of triethylamine in the ratios shown in the table below. The reaction mixtures were flushed with $N_2$ for 5 minutes, heated to reflux under $N_2$, cooled to 0° C. and filtered. The recovered crystals were washed twice with 5 ml MeOH and air dried to yield white crystals.

TABLE 1

| Starting Materials | [Ru(P(C$_6$H$_5$)$_3$)$_2$Cl$_2$]$_2$ | MeOH | NEt$_3$ | Reaction time | Products | Hydrocodone/codeine/neopine (area % by HPLC) |
|---|---|---|---|---|---|---|
| Codeine 1.0 g | 10 mg | 5 ml | 0.25 ml | 2 h | 0.85 g | 96.7/1.8/0.33 |
| Codeine 1.0 g | 10 mg | 5 ml | 0.25 ml | 3 h | 0.99 g | 94.7/0/0 |
| Codeine 2.5 g | 25 mg | 12.5 ml | 0.725 ml | 3 h | 1.58 g | 100/0/0 |
| Codeine 1 g/ Codeine. sulfate 0.05 g | 10 mg | 5 ml | 0.25 ml | 3 h | 0.61 g | 97.4/1.0/0 |
| Codeine 1 g/ CodeineHCL 0.05 g | 55 mg | 10 ml | 0 | 3 h | 1.17 g | 77.5/2.5/0.8 |
| CodeineHCl 1.1 g | 100 mg | 10 ml | 0 | 15 h | 1.16 g | 81.5/11.6/0 |
| Morphine (recry) 1.0 g | 80 mg | 10 ml | 0.25 | 3 days | 1.08 g | Hydromorphone/morphine = 88.6/6.1 |

Example 5

Codeine, 5.0 g, and 0.117 g catalyst, Ru(P(C$_6$H$_5$)$_3$)$_3$Cl$_2$, were dissolved in 25 ml EtOH. The mixture was flushed with nitrogen for 5 minutes. After refluxing under nitrogen for 2 hours the reaction mixture was cooled down to 0° C. and filtered. The collected crystals were washed twice with 5 ml each MeOH and dried in air for 1 hour to yield white crystals, 70% yield hydrocodone.

Example 6

Morphine, 1.0 g, and 80 mg [Ru(P(C$_6$H$_5$)$_3$)$_2$Cl$_2$]$_2$ was suspended in 10 ml MeOH. The reaction mixture was flushed with N$_2$ for 3 minutes, after which 0.25 ml triethylamine was added, and the mixture flushed with N$_2$ for another 3 minutes. The reaction mixture was heated to reflux with stirring under N$_2$ for 72 hours. The resulting solid was found to be hydromorphone.

Example 7

Codeine, 5.09 g, 25.4 mg RuCl$_3$xH$_2$O and 95.9 mg P(C$_6$H$_5$)$_3$ were added to 25 ml ethanol in a three neck flask. The flask was flushed with N$_2$ for 5 minutes. The mixture was heated until reactants dissolved, and then refluxed, under nitrogen, overnight. The resulting solution was washed twice with 5 ml each MeOH and air dried to yield 3.31 g product. Analysis determined the presence of hydrocodone and Ru catalyst.

Example 8

Codeine-HCl, 1.1 g and 0.1 g RuCl$_2$(P(C$_6$H$_5$)$_3$)$_3$ were stirred in 10 ml MeOH and flushed with N$_2$ for 5 minutes. The reaction mixture was refluxed overnight under N$_2$, cooled to room temperature and dried under vacuum, yielding 1.16 g brown solid containing hydrocodone.

From the foregoing description those skilled in the art will appreciate that economical and efficient methods for the catalytic conversion of codeine or morphine into hydrocodone or hydromorphone, respectively, are provided.

Having described the invention in detail, those skilled in the art will appreciate that modifications may be made of the invention without departing from its spirit and scope. Therefore, it is not intended that the scope of the invention be limited to the specific embodiments described. Rather, it is intended that the appended claims and their equivalents determine the scope of the invention.

The invention claimed is:

1. A method comprising catalytically converting a compound of Formula I into a compound of Formula II utilizing at least one transition metal complex of a tertiary phosphine halide, wherein R$^1$ is H, alkyl, aryl or acyl and wherein the metal complex is of the formula [M(PR$^2_3$)$_n$X$_m$]$_p$ wherein M is a Group VIII transition metal, R$^2$ is an alkyl or aryl, X is H, a halide or halide compound, n is 1, 2, 3 or 4, p is at least 1 and m is 1 or 2

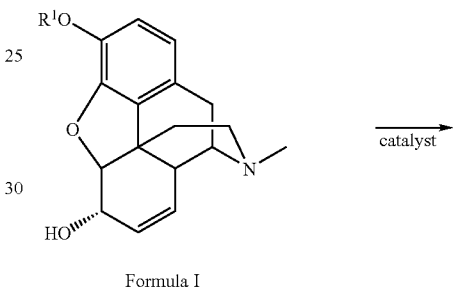

Formula I

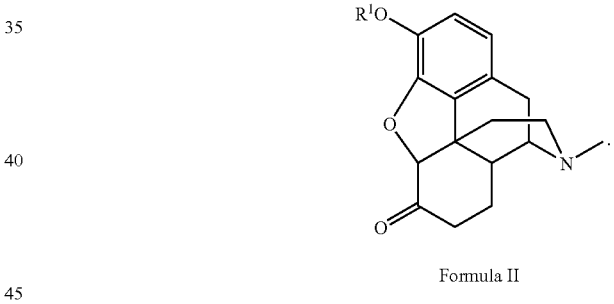

Formula II

2. The method according to claim 1 wherein R$^1$ is H or CH$_3$.

3. The method of claim 1 wherein the metal complex is of the formula [Rh(PR$^2_3$)$_n$X]$_p$, wherein R$^2$ is an alkyl or aryl, X is a halide or halide compound, n is 1, 2 or 3 and p is at least 1.

4. The method of claim 1 wherein the metal complex having the formula [Rh(PR$^2_3$)$_n$Y]$_p$, wherein n is 1, 2 or 3, p is at least 1 and Y is selected from the group consisting of BF$_4$, PF$_6$, ClO$_4$ and OCOCF$_3$.

5. The method of claim 1 wherein in the metal complex is of the formula [RuX$_2$(PR$^2_3$)$_n$]$_p$ wherein R$^2$ is an alkyl or aryl, X is a halide, n is 1, 2, 3 or 4 and p is at least 1.

6. The method of claim 1 wherein the metal complex is of the formula [RuYX(PR$^2_3$)$_n$]$_p$ wherein R$^2$ is an alkyl or aryl and wherein n=3, p is at least 1, Y=H and X=Cl; or n=3, p is at least 1, Y=H and X=H; or n=4, p is at least 1, X=H, Y=H; or n=2, 3 or 4 and X=Y is selected from the group consisting of ClO$_4$, CF$_3$SO$_3$, PF$_6$ and BF$_4$.

7. A method for producing hydrocodone comprising converting codeine into hydrocodone in the presence of at least one transition metal complex of a tertiary phosphine halide wherein the metal complex is of the formula $[M(PR^2_3)_nX_m]_p$ wherein M is a Group VIII-transition metal, $R^2$ is an alkyl or aryl, X is H, a halide or halide compound, n is 1, 2, 3 or 4, p is at least 1 and m is 1 or 2.

8. The method of claim 7 wherein the metal complex is of the formula $[Rh(PR^2_3)_nX]_p$, wherein $R^2$ is an alkyl or aryl, X is a halide or halide compound, n is 1, 2 or 3 and p is at least 1.

9. The method of claim 7 wherein the metal complex is of the formula $[Rh(PR^2_3)_nY]_p$, wherein $R^2$ is an alkyl or aryl, n is 1, 2 or 3, p is at least 1 and Y is selected from the group consisting of $BF_4$, $PF_6$, $ClO_4$ and $OCOCF_3$.

10. The method of claim 7 wherein in the metal complex is of the formula $[RuX_2(PR^2_3)_n]_p$ wherein $R^2$ is an alkyl or aryl, X is a halide, n is 1, 2, 3 or 4 and p is at least 1.

11. The method of claim 7 wherein the metal complex is of the formula $[RuYX(PR^2_3)_n]_p$ wherein $R^2$ is an alkyl or aryl and wherein n=3, p is at least 1, Y=H and X=Cl; or n=3, p is at least 1, Y=H and X=H; or n=4, X=H, Y=H; or n=2, 3 or 4, p is at least 1 and X=Y is selected from the group consisting of $ClO_4$, $CF_3SO_3$, $PF_6$ and $BF_4$.

12. A method for producing hydrocodone comprising converting codeine into hydrocodone in the presence of at least one catalyst, wherein the catalyst includes $RhCl(P(C_6H_5)_3)_3$ or $[Ru(P(C_6H_5)_3)_2Cl_2]_2$.

13. A method for producing hydromorphone comprising converting morphine into hydromorphone in the presence of at least one transition metal complex of a tertiary phosphine halide wherein the metal complex is of the formula $[M(PR^2_3)_nX_m]_p$ wherein M is a Group VIII-transition metal, $R^2$ is an alkyl or aryl, X is a halide or halide compound, n is 1, 2, 3 or 4, p is at least 1 and m is 1 or 2.

14. The method of claim 13 wherein the metal complex is of the formula $[Rh(PR^2_3)_nX]_p$, wherein $R^2$ is an alkyl or aryl, X is a halide or halide compound, n is 1, 2 or 3 and p is at least 1.

15. The method of claim 13 wherein the metal complex is of the formula $[Rh(PR^2_3)_nY]_p$, wherein $R^2$ is an alkyl or aryl, n is 1, 2 or 3, p is at least 1 and Y is selected from the group consisting of $BF_4$, $PF_6$, $ClO_4$ and $OCOCF_3$.

16. The method of claim 13 wherein in the metal complex is of the formula $[RuX_2(PR^2_3)_n]_p$ wherein $R^2$ is an alkyl or aryl, X is a halide, n is 1, 2, 3 or 4 and p is at least 1.

17. The method of claim 13 wherein the metal complex is of the formula $[RuYX(PR^2_3)_n]_p$ wherein $R^2$ is an alkyl or aryl and wherein n=3, Y=H and X=Cl; or n=3, Y=H, p is at least 1 and X=H; or n=4, p is at least 1, X=H, Y=H; or n=2, 3 or 4, p is at least 1 and X=Y is selected from the group consisting of $ClO_4$, $CF_3SO_3H$, $PF_6$ and $BF_4$.

18. A method for producing hydromorphone comprising converting morphine into hydromorphone in the presence of at least one catalyst, wherein the catalyst includes $RhCl(P(C_6H_5)_3)_3$ or $[Ru(P(C_6H_5)_3)_2Cl_2]_2$.

\* \* \* \* \*